United States Patent
Zhang et al.

(10) Patent No.: US 12,203,030 B2
(45) Date of Patent: Jan. 21, 2025

(54) METHOD FOR REDUCING PRESSURE AND INCREASING INJECTION BY CONTINUOUS OPERATION SYSTEM OF BIOLOGICAL ACID ACIDIFICATION AND NANO COATING

(71) Applicants: CHINA UNIVERSITY OF GEOSCIENCES, BEIJING, Beijing (CN); YANGTZE UNIVERSITY, Wuhan (CN)

(72) Inventors: Fan Zhang, Wuhan (CN); Yuehui She, Wuhan (CN); Qing Feng, Wuhan (CN); Xiaonan Li, Wuhan (CN); Shengsheng Li, Wuhan (CN)

(73) Assignees: CHINA UNIVERSITY OF GEOSCIENCES, BEIJING, Beijing (CN); YANGTZE UNIVERSITY, Wuhan (CN)

( * ) Notice: Subject to any disclaimer, the term of this patent is extended or adjusted under 35 U.S.C. 154(b) by 130 days.

(21) Appl. No.: 17/901,913

(22) Filed: Sep. 2, 2022

(65) Prior Publication Data
US 2024/0076538 A1   Mar. 7, 2024

(51) Int. Cl.
   *C09K 8/582*   (2006.01)
   *C09K 8/72*    (2006.01)
   *C12N 1/20*    (2006.01)
   *C12R 1/125*   (2006.01)

(52) U.S. Cl.
   CPC ........... *C09K 8/582* (2013.01); *C09K 8/72* (2013.01); *C12N 1/20* (2013.01); *C12R 2001/125* (2021.05)

(58) Field of Classification Search
   None
   See application file for complete search history.

(56) References Cited

U.S. PATENT DOCUMENTS

| | | | | |
|---|---|---|---|---|
| 4,355,109 A | * | 10/1982 | Zajic | B03D 1/004 435/249 |
| 9,452,968 B1 | * | 9/2016 | Oroskar | B01D 15/327 |
| 2016/0257975 A1 | * | 9/2016 | Lynch | C12N 9/001 |
| 2016/0289781 A1 | * | 10/2016 | Shao | C12P 17/10 |
| 2019/0161815 A1 | * | 5/2019 | Sankarakumara Pillai | C14C 1/06 |
| 2022/0127436 A1 | * | 4/2022 | Rasheed | C08L 5/08 |
| 2023/0242805 A1 | * | 8/2023 | Yan | C10L 3/108 507/90 |

* cited by examiner

*Primary Examiner* — John J Figueroa
(74) *Attorney, Agent, or Firm* — Rivkin Radler LLP

(57) ABSTRACT

Disclosed is a method for reducing pressure and increasing injection by continuous operation system of biological acid acidification and nano coating, specifically including composition and preparation method of biological acidizing agent and nano coating agent. The method for reducing pressure and increasing injection by continuous operation system of biological acid acidification and nano coating of the present disclosure is able to effectively dredge the stratum water flow channel, reduce the water flow resistance, and achieve the effect of high-efficiency pressure reduction and injection increase of the water injection well.

1 Claim, 4 Drawing Sheets

METHOD FOR REDUCING PRESSURE AND INCREASING INJECTION BY CONTINUOUS OPERATION SYSTEM OF BIOLOGICAL ACID ACIDIFICATION AND NANO COATING

TECHNICAL FIELD

The present disclosure relates to the technical field of reservoir protection, in particular to an agent system and a method for removing blocking damage of reservoir.

BACKGROUND

The reservoir is inevitably damaged due to the entry of external substances, starting from the moment when the crude oil reservoir is opened. The most important damage to the reservoir with water drive as the main mining method is the hydration swelling damage of clay minerals caused by reservoir water sensitivity, the scaling damage caused by the incompatibility of injected water and stratum, and the particle migration damage caused by water flow. The most obvious consequence of these damages is that the pressure of water injection wells increases, and the volume of water injected decreases, resulting in the lack of effective supplement of stratum energy and the decline of crude oil recovery. Many oil companies take many measures to reduce pressure and increase injection of water wells, where the main technical scheme is to remove the stratum blockage and dredge the water flow channel; as well as improve the rock wettability and reduce the water flow resistance. Acidizing operation is the main technical means to remove stratum blockage and dredge water flow channels. Chemical molecular coating and nano coating are the main means to improve rock wettability and reduce water flow resistance. These technologies have been widely used in oil fields, but they all have certain disadvantages. Sediment will inevitably be produced during the implementation of stratum blockage removal by acidizing technology, especially the mud acid compound blockage removal agent. These generated migrational sediment particles will cause secondary damage to the stratum. In the technical scheme of the molecular coating, the adsorption between chemical molecules or nanoparticles and the rock surface is mainly due to the van der Waals force between molecules, which is not strong. The coating is very easy to desorb from the rock surface under the scouring of a certain water flow. These disadvantages make the effectiveness of acidizing blockage removal and molecular coating in reducing pressure and increasing injection in oil fields not long. Most water injection wells, especially high displacement water injection wells, need frequent blockage removal operations, which greatly increases the cost of crude oil production.

In a large number of reported studies and field tests, acidizing blockage removal and coating technology are applied separately according to the analysis results of blocking factors and physical properties of oil reservoir, and there are few studies and field process reports on the feasibility of the combined application of the two technologies and the relationship between the two technologies. The study of mineral basis shows that the amount and intensity of mineral adsorbed nanoparticles, depend on the amount (i.e. number) of charges of minerals. The firmness of adsorbed particles depends on the density of charges on the mineral surface. The change of charge of clay minerals is related to the solubility of acid to minerals. At present, the most commonly used acid that may interact with minerals in oil fields is a mud acid system composed of hydrochloric acid and hydrofluoric acid. Mud acid shows strong solubility to minerals, and the reaction speed between mud acid and minerals is too fast. Therefore, it is easy to form a passivation layer on the surface of minerals, which hinders the continuation of the role of acid salts. At the same time, the secondary sediment generated is difficult to dissolve, causing secondary damage to the reservoir. Biological acid is a low molecular weight compound containing one or more carboxyl functional groups. The ability of biogenic organic acids to dissolve minerals due to $H^+$ and the ligands of radicals of organic acids under acidic pH conditions. The introduction of organic acids greatly increases the dissolution rate of minerals. The process of organic acid acidification may effectively change the charge amount of rock minerals, which may effectively increase the adsorption of nanoparticle rocks.

Low molecular weight organic acids may be synthesized by microbial fermentation. The high dissolution rate of biological acid molecules to minerals and technology of producing biological acid by microorganisms from waste resources may greatly improve the effect of oilfield acidification and blockage removal, reduce the operation cost of oilfield acidizing field, and has a good application prospect. At the same time, due to the advantages of low cost, the same composition with rocks and minerals of stratum, good compatibility with stratum and green environmental protection, modified nano silica particles are the most used nano agents in oil fields.

The degree of dissolution in the biological acid acidification process of reservoir determines the amount of surface charges of minerals, the amount (i.e. number) of mineral charges determines the amount of adsorption of minerals on nanoparticles and the density of adsorption film, and the density of nano coating determines the effect of pressure reduction and injection increase of the process and scouring resistance of the nano coating. Therefore, the present disclosure provides a new system and process scheme for reducing pressure and increasing injection by continuous operation system of biological acid acidification and nano coating. Biological acid produced by microbial fermentation is used as the main acidifier and the modified hydrophobic nano silica is used as the main nano coating agent, forming a continuous operation system of biological acid acidification and nano coating to achieve the effect of high-efficiency pressure reduction and injection increase in water injection wells.

At present, there is no report on the detailed technical principle and field application of the combined application of biological acid acidification and nano coating technology.

SUMMARY

In view of the absence of the foregoing agent system and process scheme in the prior art, the present disclosure provides a method for reducing pressure and increasing injection by continuous operation system of biological acid acidification and nano coating, where specifically including composition and preparation method of biological acidizing agent and nano coating agent, and a method for reducing pressure and increasing injection by continuous operation system of biological acid acidification and nano coating.

The present disclosure provides a biological acidizing agent, including 50-80 parts of cell-free biological acid fermentation broth, 15-20 parts of cell-free biosurfactant fermentation broth, 5-10 parts of sodium gluconate, 5-10 parts of potassium chloride and 1-5 of parts antibacterial agent.

The present disclosure provides a nano coating agent, including 1-5 of parts hydrophobic nano $SiO_2$, 50-80 of parts cell-free biosurfactant fermentation broth, 15-30 of parts sodium citrate and 1-5 parts of alcohol additives by mass.

In one embodiment, fermentation bacteria of the biological acid fermentation broth are selected from any three or more of *Klebsiella oxytoca, Bacteroides acidifaciens, Geobacillus thermoglucosidasius, Bacillus subtilis, Enterobacter mori* and *Paenibacillus*.

In one embodiment, a fermentation condition of the biological acid fermentation broth is molasses 5%, $(NH_4)_2HPO_4$ 0.1%, NaCl 1%, pH 7.2, inoculum amount 5%, fermentation temperature 37° C., fermentation for 5 days.

In one embodiment, fermentation bacteria of the biosurfactant fermentation broth is selected from any one or more of *Brevibacillus borstelensis, Brevibacillus agri* and *Bacillus flexus*.

In one embodiment, a fermentation condition of the biosurfactant fermentation broth is sucrose 20%, sodium glutamate 7%, $KH_2PO_4$ 6.8%, KCl 0.5%, pH 7.2, inoculum amount 5%, fermentation temperature 37° C., fermentation for 5 days.

In one embodiment, a method for preparing the cell-free fermentation broth includes adding 0.1-0.5% sodium alginate and subsiding for 12 hours, followed by filtering with rotary vacuum disk-filter.

In one embodiment, the alcohol additives include ethylene glycol, propylene glycol and butanediol.

The present disclosure provides a method for preparing the biological acidizing agent, where including the following steps:

step a): adding 50-80 parts of cell-free biological acid fermentation broth and 15-20 parts of cell-free biosurfactant fermentation broth into a reaction kettle, and stirring for 60-80 minutes at 45° C., 200 RPM;

step b): adding 5-10 parts of sodium gluconate and 5-10 parts of potassium chloride to the reaction kettle, stirring for 20 minutes, cooling to room temperature, and standing for 2 hours to obtain the biological acidizing agent.

The present disclosure further provides a method for preparing the nano coating agent, where including the following steps:

step A): adding 1-5 parts of hydrophobic nano $SiO_2$ and 1-5 parts of alcohol additives into a reaction kettle, soaking for 30 minutes;

step B): adding 50-85 parts of cell-free biosurfactant fermentation broth and 15-25 parts of sodium citrate, stirring for 90-120 minutes at 60-80° C., 200 RPM.

The present disclosure provides a method for reducing pressure and increasing injection by continuous operation system of biological acid acidification and nano coating, where including the following steps:

step i): determining the 1 PV injected:

$$1PV=\pi R^2 H\emptyset$$

R=treatment radius (m), H=thickness of water absorbing layer, Ø=average porosity of stratum step ii): carrying out continuous operation procedure of biological acid acidified nano film coating: stopping injecting water into water injection well, injecting 1.5-3 PV of 2% KCl solution into wellhead of the water injection well at a rate of 5-20 m³/h, injecting 1.8-5 PV of 33% biological acidizing agent into wellhead of the water injection well, injecting 0.5-1.5 PV of 2% KCl solution and 10-20 m³ water in sequence, shutting down the water injection well for 6-18 hours, injecting 1-2.5 PV of 10% nano coating agent, then injecting 20-30 m³ water, resuming water injection in the water injection well after 48-72 hours of shut-in well.

Compared with the prior art, the present disclosure has the advantages of:

1. The biological acid acidifying agent of the present disclosure is the cell-free microbial acid producing fermentation broth, which is a multi-component biological acid mixture, has high-efficiency corrosion effect, and is capable of effectively removing the blockage of the inorganic scale in the stratum.

2. The nano coating agent of the present disclosure is a biosurfactant nano dispersion system. Cell-free biosurfactant fermentation broth produced by microorganisms is able to efficiently disperse nanoparticles, forming a stable nano dispersion system. At the same time, the biosurfactant is able to emulsify and disperse the organic scale of the stratum and remove the blockage of the organic scale in the stratum.

3. The process described in the present disclosure is a continuous operation process of biological acid acidification and nano coating, which is capable of effectively making up for the defects of the use of a separate process. The advantages of blockage removal and injection increase of the two processes of biological acid acidification and nano coating are synergistic effect, which realizes the effect of process 1+1>2.

4. The components of the biological acidizing agent and the nano film coating agent are biological products, which may be degraded by microorganisms and have no potential environmental hazards.

DETAILED DESCRIPTION OF THE DISCLOSURE

Figure 1:
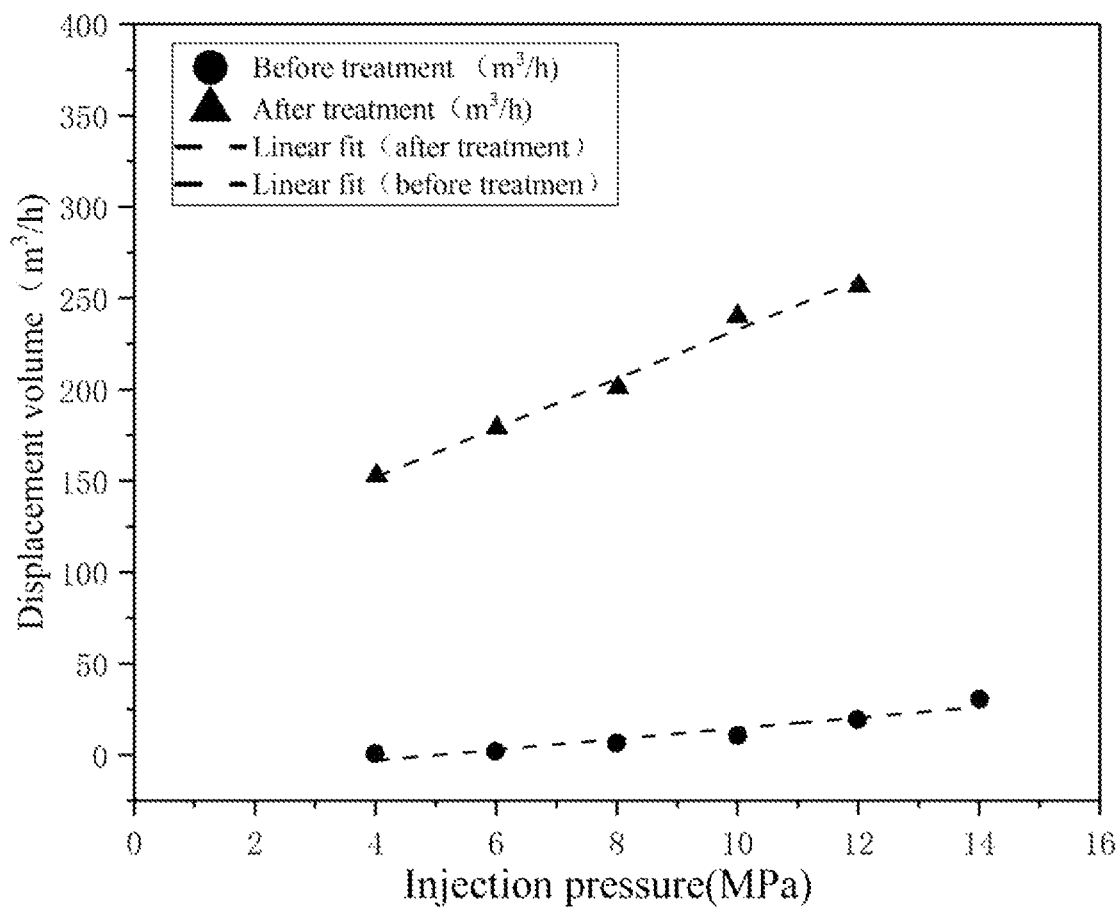
FIG. 1 shows a water absorption curve of well 1# before and after treatment in accordance with an embodiment of the disclosed system and method.

In order to better understand the above purposes, features and advantages of the present disclosure, the present disclosure is further described in detail below in combination with specific embodiments. It should be noted that the embodiments of the present disclosure and the features in the embodiments can be combined with each other without conflict.

Example 1

The biological acid acidifying agent included 80 parts of cell-free biological acid fermentation broth of *Bacteroides acidifaciens, Geobacillus thermoglucosidasius* and *Bacillus subtilis* (mixed acid), 10 parts of cell-free biosurfactant fermentation broth of *Brevibacillus borstelensis* and *Brevibacillus agri*, 5 parts of sodium gluconate and 5 parts of potassium chloride by mass. The above proportion of cell-free biological acid fermentation broth and cell-free biosurfactant fermentation broth were added to the reaction kettle to stir for 80 minutes at 45° C., 200 RPM. The sodium gluconate and potassium chloride were added to the reaction kettle to stir for 20 minutes to obtain a mixture. The mixture was cooled to room temperature and stood for 2 hours to obtain the biological acidizing agent 1.

The nano coating agent included 1.2 parts of hydrophobic nano $SiO_2$, 80 parts of cell-free biosurfactant fermentation broth of *Brevibacillus borstelensis* and *Brevibacillus agri*, 15 parts of sodium citrate and 3.8 parts of alcohol additives by mass. The above proportion of hydrophobic nano $SiO_2$ and alcohol additives were added to the reaction kettle to soak for 30 minutes. The cell-free biosurfactant fermentation broth and sodium citrate were added to the reaction kettle to stir for 100 minutes at 70° C., 200 RPM to obtain the nano coating agent 1.

The continuous operation process of biological acid acidification and nano film coating was implemented for well 1#. The thickness of water injection layer of well 1# was 38.3 m, the average porosity was 20.5%, and the estimated treatment radius was 1.2 m. It was calculated that 1 PV was 35.50 m³ according to $$1PV=\pi R^2 H \varnothing.$$

The continuous operation procedure of biological acid acidified nano film coating was carried out. The water injection in water injection well 1# was stopped. 2.25 PV of 2% KCl solution was injected into wellhead of the water injection well at a rate of 615 m³/d 3.95 PV of 33% biological acidizing agent was injected into wellhead of the water injection well. 1.1 PV of 2% KCl solution and 20 m³ of water were injected in sequence. The water injection well was shut down. 1.1 PV of 10% nano coating agent and 30 m³ of water were injected in sequence after 12 hours. The water injection well was shut down. The water injection in the water injection well was resumed after 72 hours.

The displacement volume of well 1# before treatment is 31 m³/d, and the injection pressure is 14.5 MPa. After treatment by the continuous operation process of biological acid acidification and nano coating, the injection volume is 260 m³/d, the injection pressure is 12.5 MPa, the injection pressure decreases by 2 MPa and the injection volume increases to 8-fold. The apparent water absorption index after treatment is 9.7 times of that before treatment (FIG. 1).

Example 2

The biological acid acidifying agent included 70 parts of cell-free biological acid fermentation broth of *Klebsiella Oxytoca, Bacteroides acidifaciens* and *Enterobacter mori* (mixed acid), 15 parts of cell-free biosurfactant fermentation broth of *Brevibacillus borstelensis* and *Bacillus flexus*, 10 parts of sodium gluconate and 5 parts of potassium chloride by mass. The above proportion of cell-free biological acid fermentation broth and cell-free biosurfactant fermentation broth were added to the reaction kettle to stir for 60 minutes at 45° C., 200 RPM. The sodium gluconate and potassium chloride were added to the reaction kettle to stir for 20 minutes to obtain a mixture. The mixture was cooled to room temperature and stood for 2 hours to obtain the biological acidizing agent 2.

The nano coating agent included 1.3 parts of hydrophobic nano $SiO_2$, 80 parts of cell-free biosurfactant fermentation broth of *Brevibacillus borstelensis* and *Bacillus flexus*, 20 parts of sodium citrate and 3.7 parts of alcohol additives by mass. The above proportion of hydrophobic nano $SiO_2$ and alcohol additives were added to the reaction kettle to soak for 30 minutes. The cell-free biosurfactant fermentation broth and sodium citrate were added to the reaction kettle to stir for 120 minutes at 80° C., 200 RPM to obtain the nano coating agent 2.

The continuous operation process of biological acid acidification and nano film coating was implemented for well 2#. The thickness of water injection layer of well 2# was 59.6 m, the average porosity was 20.5%, and the estimated treatment radius was 1 m. It was calculated that 1 PV was 38.36 m³ according to $$1PV=\pi R^2 H \varnothing.$$

The continuous operation procedure of biological acid acidified nano film coating was carried out. The water injection in water injection well 2# was stopped. 0.78 PV of 2% KCl solution was injected into wellhead of the water injection well at a rate of 19 m³/h. 1.96 PV of 33% biological acidizing agent 2 was injected into wellhead of the water injection well. 0.52 PV of 2% KCl solution and 20 m³ of water were injected in sequence. The water injection well was shut down. 1.56 PV of 10% nano coating agent 2 and 30 m³ of water were injected in sequence after 12 hours. The water injection well was shut down. The water injection in the water injection well was resumed after 72 hours.

Figure 2:
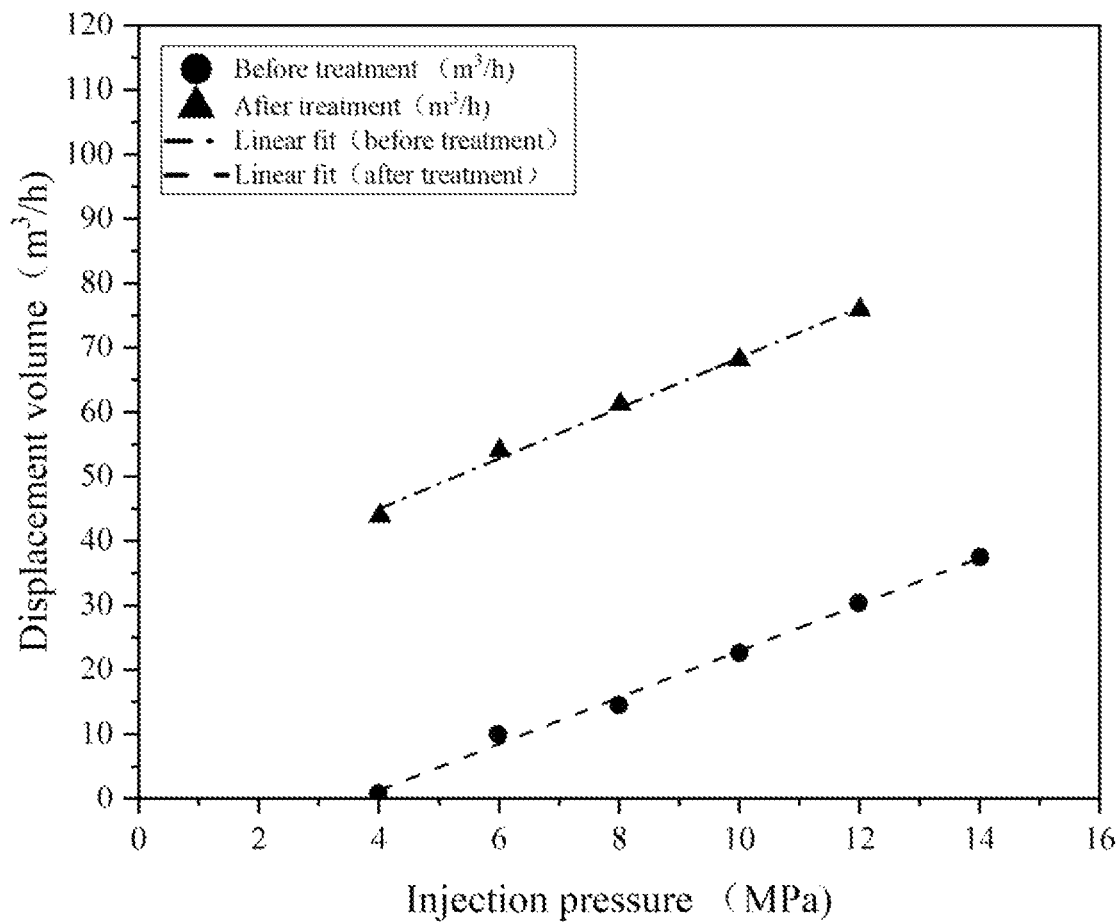
FIG. 2 shows a water absorption curve of well 2# before and after treatment in accordance with an embodiment of the disclosed system and method.

The displacement volume of well 2# before treatment is 325 m³/d, and the injection pressure is 10 MPa. After treatment by the continuous operation process of biological acid acidification and nano coating, the injection volume is 325 m³/d, the injection pressure is 0.1 MPa, the injection pressure decreases by 10 MPa. The apparent water absorption index after treatment is 92.3 times of that before treatment (shown in FIG. 2).

Example 3

The biological acid acidifying agent included 80 parts of cell-free biological acid fermentation broth of *Geobacillus thermoglucosidasius, Enterobacter mori* and *Paenibacillus* (mixed acid), 10 parts of cell-free biosurfactant fermentation broth of *Brevibacillus agri* and *Bacillus flexus*, 5 parts of sodium gluconate and 5 parts of potassium chloride by mass. The above proportion of cell-free biological acid fermentation broth and cell-free biosurfactant fermentation broth were added to the reaction kettle to stir for 80 minutes at 45° C., 200 RPM. The sodium gluconate and potassium chloride were added to the reaction kettle to stir for 20 minutes to obtain a mixture. The mixture was cooled to room temperature and stood for 2 hours to obtain the biological acidizing agent 3.

The nano coating agent included 1.5 parts of hydrophobic nano $SiO_2$, 80 parts of cell-free biosurfactant fermentation broth of *Brevibacillus agri* and *Bacillus flexus*, 15 parts of sodium citrate and 3.5 parts of alcohol additives by mass. The above proportion of hydrophobic nano $SiO_2$ and alcohol additives were added to the reaction kettle to soak for 30 minutes. The cell-free biosurfactant fermentation broth and sodium citrate were added to the reaction kettle to stir for 120 minutes at 60° C., 200 RPM to obtain the nano coating agent 3.

The continuous operation process of biological acid acidification and nano film coating was implemented for well 3#. The thickness of water injection layer of well 3# was 28.9 m, the average porosity was 21.4%, and the estimated treatment radius was 1.2 m. It was calculated that 1 PV was 27.96 m³ according to $$1PV=\pi R^2 H \varnothing.$$

The continuous operation procedure of biological acid acidified nano film coating was carried out. The water injection in water injection well 3# was stopped. 3.56 PV of 2% KCl solution was injected into wellhead of the water injection well at a rate of 18 m³/h. 4.3 PV of 33% biological acidizing agent 3 was injected into wellhead of the water injection well. 0.72 PV of 2% KCl solution and 20 m³ of water were injected in sequence. The water injection well was shut down. 2.15 PV of 10% nano coating agent 3 and 30 m³ of water were injected in sequence after 12 hours. The water injection well was shut down. The water injection in the water injection well was resumed after 72 hours.

Figure 3:
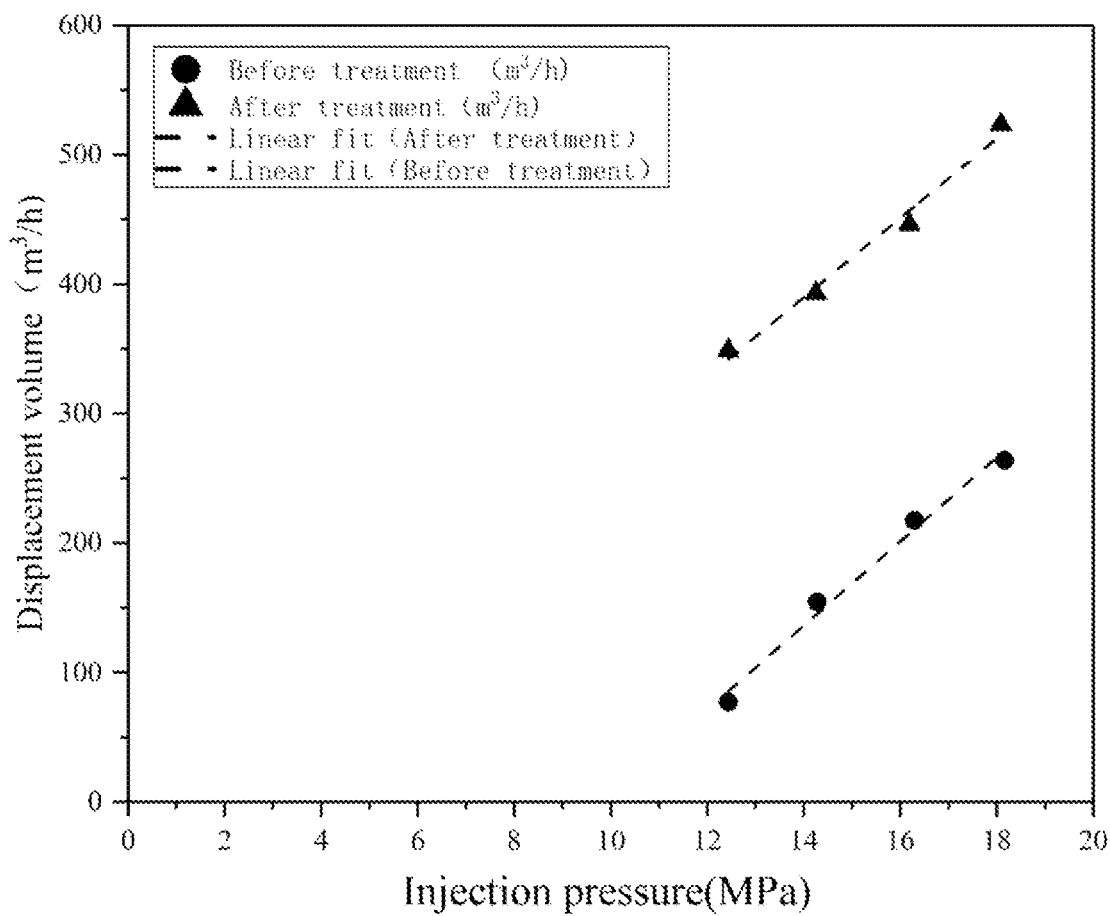
FIG. 3 shows a water absorption curve of well 3# before and after treatment in accordance with an embodiment of the disclosed system and method.

The displacement volume of well 3# before treatment is 216 m³/d, and the injection pressure is 17 MPa. After treatment by the continuous operation process of biological acid acidification and nano coating, the injection volume is 250 m³/d, the injection pressure is 6.8 MPa, the injection pressure decreases by 10 MPa. The apparent water absorption index after treatment is 2.9 times of that before treatment (shown in FIG. 3).

Example 4

The biological acid acidifying agent included 75 parts of cell-free biological acid fermentation broth of *Bacteroides acidifaciens*, *Geobacillus thermoglucosidasius* and *Enterobacter mori* (mixed acid), 15 parts of cell-free biosurfactant fermentation broth of *Brevibacillus borstelensis*, *Brevibacillus agri* and *Bacillus flexus*, 5 parts of sodium gluconate and 5 parts of potassium chloride by mass. The above proportion of cell-free biological acid fermentation broth and cell-free biosurfactant fermentation broth were added to the reaction kettle to stir for 80 minutes at 45° C., 200 RPM. The sodium gluconate and potassium chloride were added to the reaction kettle to stir for 20 minutes to obtain a mixture. The mixture was cooled to room temperature and stood for 2 hours to obtain the biological acidizing agent 4.

The nano coating agent included 1.5 parts of hydrophobic nano $SiO_2$, 70 parts of cell-free biosurfactant fermentation broth of *Brevibacillus borstelensis*, *Brevibacillus agri* and *Bacillus flexus*, 25 parts of sodium citrate and 3.5 parts of alcohol additives by mass. The above proportion of hydrophobic nano $SiO_2$ and alcohol additives were added to the reaction kettle to soak for 30 minutes. The cell-free biosurfactant fermentation broth and sodium citrate were added to the reaction kettle to stir for 100 minutes at 60° C., 200 RPM to obtain the nano coating agent 4.

The continuous operation process of biological acid acidification and nano film coating was implemented for well 4#. The thickness of water injection layer of well 4# was 58.9 m, the average porosity was 21.2%, and the estimated treatment radius was 1 m. It was calculated that 1 PV was 56.46 m³ according to $$1PV = \pi R^2 H \varnothing.$$

The continuous operation procedure of biological acid acidified nano film coating was carried out. The water injection in water injection well 4# was stopped. 0.71 PV of 2% KCl solution was injected into wellhead of the water injection well at a rate of 19 m³/h. 2.04 PV of 33% biological acidizing agent 4 was injected into wellhead of the water injection well. 0.71 PV of 2% KCl solution and 20 m³ of water were injected in sequence. The water injection well was shut down. 1.42 PV of 10% nano coating agent 4 and 30 m³ of water were injected in sequence after 12 hours. The water injection well was shut down. The water injection in the water injection well was resumed after 72 hours.

Figure 4:
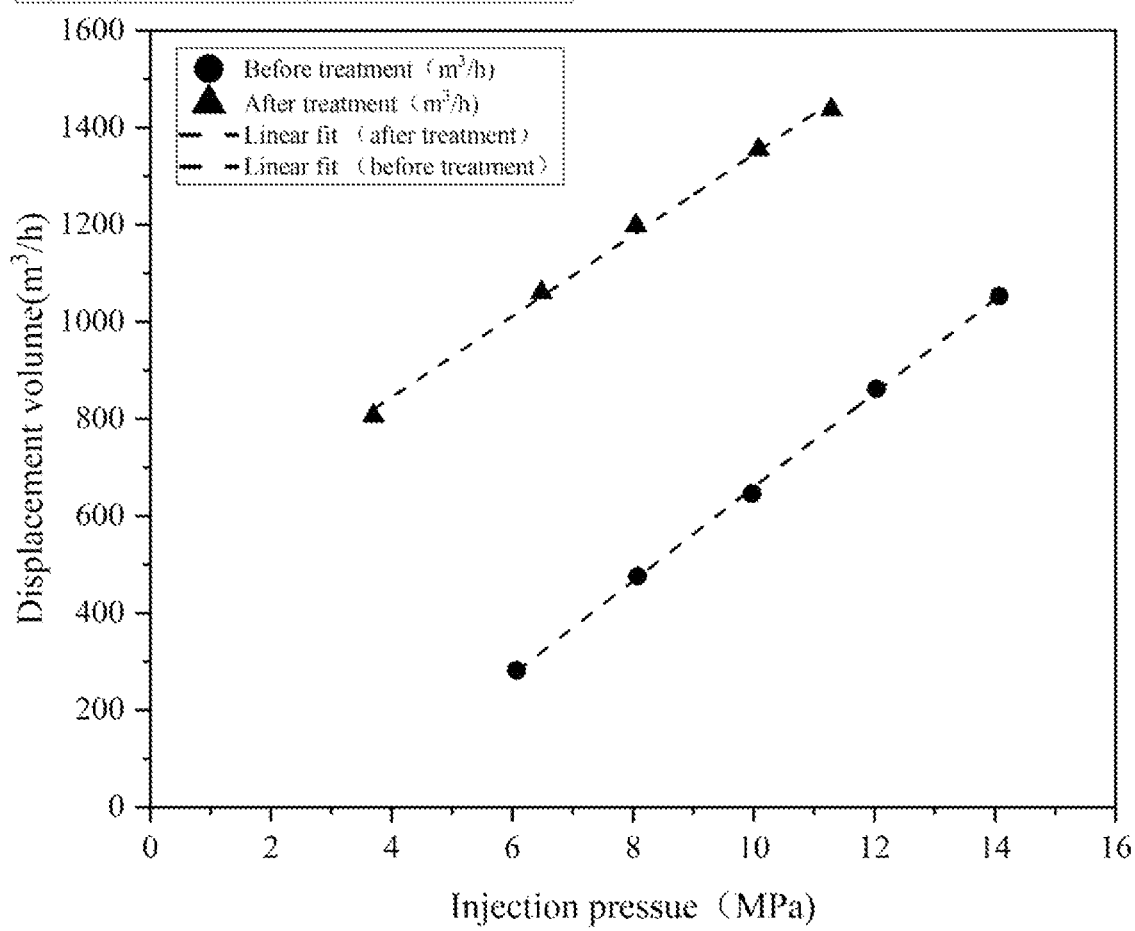
FIG. 4 shows a water absorption curve of well 4# before and after treatment in accordance with an embodiment of the disclosed system and method.

The displacement volume of well 4# before treatment is 210 m³/d, and the injection pressure is 12 MPa. After treatment by the continuous operation process of biological acid acidification and nano coating, the injection volume is 210 m³/d, the injection pressure is 1 MPa, the injection pressure decreases by 11 MPa. The apparent water absorption index after treatment is 87.6 times of that before treatment (shown in FIG. 4).

The biological acid blockage removal agent and nano coating agent prepared in the above examples 1-4 were applied to 4 water injection wells according to the method for reducing pressure and increasing injection by continuous operation system of biological acid acidification and nano coating. The effects of pressure reduction and injection increase were shown in Table 1 hereinbelow:

TABLE 1

| Examples | Wells | Thickness of water injection layer | Injection pressure Before treatment | Injection pressure After treatment | Displacement volume Before treatment | Displacement volume After treatment | Increase times of water absorption index After treatment/Before treatment |
|---|---|---|---|---|---|---|---|
| 1 | 1# | 38.3 | 15 | 12.5 | 24 | 260 | 9.7 |
| 2 | 2# | 59.6 | 10 | 0.5 | 325 | 325 | 92.3 |
| 3 | 3# | 28.9 | 16 | 6.8 | 209 | 250 | 2.9 |
| 4 | 4# | 58.9 | 12 | 1 | 210 | 210 | 88.2 |

The biological acid blockage removal agent and nano coating agent prepared in the present disclosure are mainly composed of biological acids and biosurfactants produced by microorganisms and hydrophobic nano silica, and are carried out according to the method for reducing pressure and increasing injection by continuous operation system of biological acid acidification and nano coating. The injection pressure is reduced after treatment, with the maximum decrease of 11 MPa. The displacement volume of water injection wells increased, with the largest increase of 236 m³/h. The method for reducing pressure and increasing injection by continuous operation system of biological acid acidification and nano coating can significantly increase the water absorption index of water injection wells, with the largest increase of 92.3 times. The examples show that the biological acid blockage removal agent, nano coating agent and the method for reducing pressure and increasing injection by continuous operation system of biological acid acidification and nano coating have broad application prospects for use in pressure reduction and injection increase in water injection wells.

Although specific example embodiments have been described, it will be evident that various modifications and changes may be made to these embodiments without departing from the broader scope of the inventive subject matter described herein. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "embodiment" merely for convenience and without intending to voluntarily limit the scope of this application to any single embodiment or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate example embodiment.

Although preferred embodiments have been described herein with reference to the accompanying drawings, it is to be understood that the disclosure is not limited to those precise embodiments and that various other changes and modifications may be affected herein by one skilled in the art without departing from the scope or spirit of the embodiments, and that it is intended to claim all such changes and modifications that fall within the scope of this disclosure.

The Abstract is provided to comply with 37 C.F.R. § 1.72(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The present disclosure is not limited by the above embodiments. The above embodiments and specifications are only to explain the principle of the technical scheme of the present disclosure. Any modifications and improvements will be made within the spirit and principles of the present disclosure, and these modifications and improvements should fall within the protection scope of the present disclosure. The scope of protection claimed by the present disclosure is defined by the appended claims.

What is claimed is:

1. A method for reducing pressure and increasing injection by a continuous operation system of biological acid acidification and a nano film coating, wherein the continuous operation system comprises the following steps:

step i):
  determining a 1 PV injected in accordance with the following formula:

$$1PV = \pi R^2 H \emptyset$$

wherein R=treatment radius (m), H=thickness of water absorbing layer, and $\emptyset$=average porosity of stratum; and step ii):
  carrying out a continuous operation procedure of the biological acid acidification and acidified nano film coating by stopping injection of water into a water injection well;
  injecting 1.5-3 PV of a 2% KCl solution into a wellhead of the water injection well at a rate of 5-20 m³/h;
  injecting 1.8-5 PV of 33% of a biological acidizing agent into the wellhead of the water injection well;
  injecting in sequence 0.5-1.5 PV of the 2% KCl solution and 10-20 m³ of water;
  shutting down the water injection well for 6-18 hours;
  injecting in sequence 1-2.5 PV of a 10% nano coating agent and 20-30 m³ of water; and
  resuming water injection in the water injection well after 48-72 hours of a shut-in well.

* * * * *